United States Patent [19]

Swartz et al.

[11] Patent Number: 5,494,030
[45] Date of Patent: Feb. 27, 1996

[54] APPARATUS AND METHODOLOGY FOR DETERMINING OXYGEN IN BIOLOGICAL SYSTEMS

[75] Inventors: Harold M. Swartz; Fuminori Goda; Tadeusz Walczak; Ke J. Liu, all of Hanover, N.H.

[73] Assignee: Trustees of Dartmouth College, Hanover, N.H.

[21] Appl. No.: 105,459

[22] Filed: Aug. 12, 1993

[51] Int. Cl.$^6$ .................................................. A61B 5/14
[52] U.S. Cl. .................. 128/632; 128/653.4; 128/653.5; 324/316
[58] Field of Search ........................... 128/653.2, 653.4, 128/654, 632; 324/316, 317, 318, 322; 436/173

[56] References Cited

U.S. PATENT DOCUMENTS

| | | | |
|---|---|---|---|
| 4,560,663 | 12/1985 | Nicksic et al. | 324/316 X |
| 4,593,248 | 6/1986 | Hyde et al. | 324/317 |
| 4,714,886 | 12/1987 | Halpern | 324/316 |
| 4,803,624 | 2/1989 | Pilbrow et al. | 324/316 |
| 5,204,628 | 4/1993 | Kunishi et al. | 324/316 |
| 5,233,303 | 8/1993 | Bales et al. | 324/316 |

FOREIGN PATENT DOCUMENTS

WO92/07259  4/1992  WIPO.

OTHER PUBLICATIONS

Crepeau et al., "Communications—Composite Pulses in Time–Domain ESR", *J. of Magnetic Resonance*, vol. 84, pp. 184–190 (Aug. 1989).

Glockner et al., "In Vivo Oximetry Using a Nitroxide–Liposome System", J. of Magnetic Resonance, vol. 20, pp. 123–133 (Jul. 1991).

Duret et al., "Oxygen concentration measurements using the ESR line modification of PcLi molecules", *Sensors and Actuators B Chemical*, vol. B6, pp. 266–269 (Jan. 1992).

Smirnov et al., "Simultaneous Multi-Site EPR Spectroscopy in Vivo", *Magnetic Resonance in Medicine*, vol. 30, pp. 213–220 (Aug. 1993).

Swartz et al., "India Ink" A Potential Clinically Applicable EPR Oximetry Probe, *Magnetic Resonance in Medicine*, vol. 31, pp. 229–232 (Feb. 1994).

H. M. Swartz et al., "Measurements of Pertinent Concentrations of Oxygen in Vivo", Magnetic Resonance in Medicine, pp. 333–339, vol. 20, No. 2, Aug. 1991.

K. J. Liu et al., "Lithium phthalocyanine: A probe for electron paramagnetic resonance oximetry in viable biological systems", Proceedings of the National Academy of Sciences, pp. 5438–5442, vol. 90, No. 12, Jun. 1993.

J. M. Vanderkooi et al., "Oxygen in mammalian tissue: methods of measurement and affinities of various reactions", American Journal of Physiology, pp. C1131–C1150, vol. 260, No. 6, Jun. 1991.

James F. Glockner et al., "In Vivo EPR Oximetry Using Two Novel Probes: Fusinite and Lithium Phthalocyanine", Oxygen Transport to Tissue XIV, pp. 229–234, Plenum Press, New York, 1992.

Ernst Epstein, "Surgical Gem", The Journal of Dermatologic Surgery and Oncology, pp. 273–274, vol. 15, No. 3, Mar. 1989.

(List continued on next page.)

*Primary Examiner*—Ruth S. Smith
*Attorney, Agent, or Firm*—Lahive & Cockfield

[57] ABSTRACT

The invention provides apparatus and methods for measuring oxygen tensions in biological systems utilizing physiologically acceptable paramagnetic material, such as India ink or carbon black, and electron paramagnetic resonance (EPR) oximetry. India ink is introduced to the biological system and exposed to a magnetic field and an electromagnetic field in the 1–2 GHz range. The EPR spectra is then measured at the biological system to determine oxygen concentration. The EPR spectra is determined by an EPR spectrometer that adjusts the resonator to a single resonator frequency to compensate for movements of the biological system, such as a human or animal. The biological system can also include other in vivo tissues, cells, and cell cultures to directly measure $pO_2$ non-destructively.

18 Claims, 9 Drawing Sheets

OTHER PUBLICATIONS

H. M. Swartz et al., "The Use of EPR for the Measurement of the Concentration of Oxygen in Vivo in Tissues under Physiologically Pertinent Conditions and Concentrations", The Journal of Dermatologic Surgery and Oncology, pp. 221–228, vol. 15, No. 3, Mar. 1989.

Arie H. Bartal et al., "Malignant melanoma arising at tattoo sites used for radiotherapy field marking", The British Journal of Radiology, pp. 913–914, vol. 53, No. 633, Sep. 1980.

M. Brian Fennerty et al., "Effectiveness of India Ink as a Long–term Colonic Mucosal Marker", The American Journal of Gastroenterology, pp. 79–81, vol. 87, No. 1, Jan. 1992.

William J. Whalen et al., "Skeletal muscle PO2: effect of inhaled and topically applied O2 and CO2", American Journal of Physiology, pp. 973–980.

Thomas E. J. Gayeski et al., "Intracellular PO2 in long axis of individual fibers in working dog gracillis muscle", The American Journal of Physiology, pp. H1179–H1186.

J. D. Chapman, "Measurement of tumor hypoxia by invasive and non–invasive procedures: a review of recent clinical studies", Radiotherapy and Oncology, pp. 13–19, Suppl. 20, (1991).

APPARATUS AND METHODOLOGY FOR DETERMINING OXYGEN IN BIOLOGICAL SYSTEMS

GOVERNMENT SUPPORT

This invention was made in part with government support under contract numbers NIH/GM34250 and RR01811 awarded by the National Institute of Health. The government has certain limited rights in the invention.

FIELD OF THE INVENTION

This invention relates generally to apparatus and methods for determining oxygen tension in biological systems. More particularly, the invention concerns apparatus and methods for determining oxygen tension in biological in vivo tissue utilizing physiologically acceptable paramagnetic materials and electron paramagnetic resonance oximetry.

BACKGROUND OF THE INVENTION

Benefits derived from the measurement of oxygen concentrations in tissue are known. Oxygen is the primary biological oxidant, and the measurement of oxygen tension $pO_2$ (positive pressure of oxygen) can improve the evaluation and understanding of many physiological, pathological, and therapeutic processes.

Prior art systems and methods for measuring oxygen concentrations in tissue are also known, including: the Clark electrode, fluorescence quenching, $O_2$ binding to myoglobin and hemoglobin, chemiluminescence, phosphoresence quenching, and spin label oximetry. However, these systems and methods have certain, and often acute, limitations, especially when used in vivo. They especially lack the qualities required for complete experimental and clinical use, such as sensitivity, accuracy, repeatability, and adequate spatial resolution. See J. Chapman, *Radiother. Oncol.* 20, 13 (1991) and J. M. Vanderkooi et al., "Oxygen in Mammalian Tissue: Methods of Measurement and Affinities of Various Reactions", *Am. J. Physiol.* 260, C1131 (1991).

The polarographic microelectrode is one popular device for measuring oxygen tension in tissue. However, it has obvious technical difficulties associated with the repeated insertion of the microelectrode into the tissue. For example, the microelectrode often damages the tissue, and there is repeated difficulty in re-positioning the microelectrode at the same test location. The microelectrode is also relatively insensitive to oxygen concentrations below 10 mm Hg, which is within the required sensitivity region for effective oximetry. Finally, the microelectrode may itself consume oxygen, thereby altering its own environment, inducing measurement errors, and reducing the accuracy and usefulness of the evaluation process.

There are scattered reports which concern in vivo $pO_2$ measurements with such devices, especially in skeletal muscle. Whalen and Nair, *Am. J. Physiol.* 218, 973 (1970), measured $pO_2$ of cat gracilis at rest using a recessed Au 1–51 µm microelectrode, giving average $pO_2$ values of 6.6±0.4 mm Hg (n=372). Gayeski et al., *Am. J. Physiol.* 254, H1179 (1988), measured $pO_2$ of dog gracilis at rest, exhibiting a partial pressure range of 4.5–35 mm Hg (16.8 mm Hg median), and 95% $VO_2$ max, using a Mb saturation technique, exhibiting a partial pressure range of 0.2–2.3 mm Hg (0.9–1.8 range of mean). Nevertheless, there are effective limitations to these $pO_2$ measurement techniques. In the microelectrode method, for example, it is technically difficult to monitor or make long term evaluations of $pO_2$. In the Mb saturation method, it is especially difficult to measure low $pO_2$, and the method can only be used in muscle.

Nuclear Magnetic Resonance (NMR) techniques have been explored and considered in the context of oxiometric measurements, especially through the use of an oxygen dependent proton hyperfine line in myoglobin and oxygen dependent relaxation of fluorine nuclei. NMR is a common spectroscopic technique in which the molecular nuclei is aligned in a magnetic field and simultaneously excited by absorption of radiofrequency energy. The molecular relaxation from the excited state to the initial state is an observable event that is affected by the presence of oxygen through exchange or dipolar actions. However, the NMR techniques have not demonstrated sufficient sensitivity and/or applicability to the measure of $pO_2$ in either experimental or clinical settings.

Electron Paramagnetic Resonance (EPR) oximetry is another technique for measuring oxygen tension. Similar to NMR, EPR oximetry is a spectroscopic technique based upon the Zeeman effect and the line-broadening effect of molecular oxygen on the EPR spectra of paramagnetic materials. These materials have unpaired electron spins that are aligned in a magnetic field and excited by microwave energy. The separation between the lower, unexcited energy state and the higher, excited energy state is proportional to the strength of the magnetic field. The presence of oxygen with the excited molecule measurably affects the molecular relaxation so that the line width of the EPR spectra changes and provides an indication of $pO_2$.

Nitroxides exemplify one family of compounds having paramagnetic quality that are suitable for EPR oximetry, and which have been used in a variety of in vitro experiments. Although nitroxides have also been tested in vivo, at least two resulting problematic areas exist in such measurements: first, nitroxides tend to be bioreduced; and secondly, nitroxides are relatively insensitive to low oxygen tension levels that are of the most biological interest today, i.e., less than 10 mmHg.

Other recent discoveries of new paramagnetic materials, such as Fusinite and lithium phthalocyanine (LiPc), have made progress as oxygen probes in the field of in vivo EPR oximetry. These two compounds, for example, are suitable for in vivo usage because they exhibit certain favorable characteristics, including: accuracy; spatial resolution; sensitivity in the physiologically important oxygen tension range; ease of use; little or no apparent toxicity; and relative stability in tissues, permitting prolonged measurements over periods of weeks or months after administering the compound. Nevertheless, because these paramagnetic compounds have not been previously tested in humans, they will have to undergo very long and extensive toxicological evaluation before they can be used clinically. This evaluation is likely to be prolonged because of other problems inherent in the compounds, such as stability and inertness, which encourage indefinite, unwanted persistence within the tissue.

There are other existing problems limiting the effectiveness of EPR oximetry, including the inability to measure EPR spectra efficiently and effectively, especially in vivo. Conventional EPR spectrometers, for example, typically utilize microwave frequencies, e.g., 9 GHz, that are strongly absorbed by tissue and water, and which reduce the useful depth penetration and measurement sensitivities within the tissue. Prior EPR spectrometers also cannot effectively measure EPR spectra from a biological system such as a live animal, because movements of the animal change the observed EPR spectra. This movement increases noise and reduces the accuracy. Finally, conventional EPR spectrometers have the resonator and the sample under test, e.g., tissue, within a common magnetic field. This constrains the EPR measurement/flexibility, being subject to physical size considerations, and potentially to the patient's dexterity.

It is accordingly an object of this invention to provide an improved EPR spectrometer and associated methodology that are free of the afore-mentioned difficulties.

It is another object of this invention to provide an improved apparatus and method that enables the direct measurement of oxygen concentration in biological systems, such as tissue.

It is a further object of the invention to provide improved methodology and apparatus for in vivo EPR oximetry.

Other objects of the invention will be apparent from the following description.

SUMMARY OF THE INVENTION

The invention attains these and other objects, according to one aspect, by providing a method for evaluating oxygen tensions in a biological system, including the steps of (1) introducing physiologically acceptable paramagnetic material to the biological system, (2) applying a magnetic field and an electromagnetic field to the biological system, and (3) determining the EPR spectra of the biological system. The paramagnetic material is of the type which has an EPR spectra responsive to the presence of oxygen, such as India ink, constituents of India ink having paramagnetic quality, carbon black, and other carbon-based material. The biological system includes in vivo and in vitro biological systems, biological tissues, cells, cell cultures, animals, and live human beings.

In another aspect, the method provides for the step of calibrating the EPR spectra of the paramagnetic material by comparing the EPR spectra of the biological system with the EPR spectra of the paramagnetic material in the presence of a known concentration of oxygen. Preferably, both the measured spectra from the biological system and the calibration spectra are determined by the spectra's peak-to-peak line width. The peak-to-peak line width indicates oxygen tension in the biological system, and oxygen concentration is determined directly by comparing the measured line width to the calibration line width.

In other aspects, the method provides for sweeping the magnitude of the magnetic field between approximately 100 and 500 Gauss to acquire the EPR spectra through the frequencies of the EPR resonance. The step of sweeping preferably occurs in less than 60 seconds.

In another aspect, the magnetic field includes a first magnetic field having lines of force in substantially one direction, and the method provides for applying a second magnetic field to the biological system that is substantially parallel to the first magnetic field. The second magnetic field is thereafter slowly varied to modify, or sweep, the magnitude of the first magnetic field between approximately 1 and 500 Gauss, to acquire the EPR spectra through the EPR resonance frequencies. Alternatively, an electromagnet is employed to sweep the magnetic intensities. Preferably, a third magnetic field is applied to the biological system that is substantially perpendicular to the first magnetic field. The third magnetic field is modulated between approximately 1 and 500 kHz, to improve the signal-to-noise ratio for determining the spectra. Preferably, the electromagnetic field applied to the biological system is directed substantially perpendicular to the first magnetic field with an oscillating frequency between approximately 100 MHz and 5 GHz, such as in the microwave L-band.

In still another aspect, the method includes the step of determining the EPR spectra by utilizing an EPR spectrometer that has a resonator and an associated Q factor. The Q factor is determined and monitored for change, such that, in another aspect, the Q factor is compensated to maintain resonant frequency during movements by the biological system, e.g., the tissue or animal.

The method in accordance with the invention also provides for introducing to the biological system a paramagnetic material that has substantially uniform particles with diameters between approximately 0.1 and 100 microns. Alternatively the paramagnetic material can include at least one relatively large particle with a diameter between approximately 100 microns and one centimeter. This relatively large paramagnetic particle functions as a point source to spatially determine the EPR spectra in the biological system.

In other aspects according to the invention, the paramagnetic material is introduced to the biological system by several appropriate methods. In tissue, for example, the material can be injecting directly into the biological system. If the biological system has a circulatory blood stream, the paramagnetic material can be introduced directly into the blood stream. Accordingly, the method can include the further steps of (1) changing the blood flow to the biological system or tissue, and (2) determining the change in the EPR spectra to provide a real-time evaluation of the change in oxygen concentration in the tissue. Additionally, the blood flow to the tissue can be reduced to reduce the oxygen concentration in the tissue.

The paramagnetic material can also be introduced to the biological system via lymphatics. To derive additional spatial information, the paramagnetic material can also be selectively introduced to a localized region within the biological system, thereby indicating oxygen tension at the localized region. Alternatively, the paramagnetic material is introduced to a biological system having phagocytic activity, such that the paramagnetic material is introduced to the biological system by phagocytosis.

The invention also provides for a method to determine EPR spectra of a biological system having a surface. When the biological system has a surface, e.g., the skin of an animal, the EPR spectra is preferably determined from the surface. In other aspects, an EPR resonator constructed in accordance with the invention for use with an EPR spectrometer directly measures EPR spectra from the surface.

In another aspect, a method is provided for evaluating oxygen tension in a cell. Physiologically acceptable paramagnetic material— which has an EPR spectra responsive to the presence of oxygen—is first introduced to the cell, such as through phagocytosis. A magnetic field and an electromagnetic field are then applied to the cell, and the peak-to-peak line width of the EPR spectra of the cell is determined. The paramagnetic material can include carbon black, carbon-based material, India ink, or ingredients of India ink having physiologically acceptable paramagnetic quality. The electromagnetic field preferably has a frequency between approximately 100 MHz and 5 GHz.

The method additionally provides for the steps of determining the EPR spectra peak-to-peak line width of the paramagnetic material in the presence of a known concentration of oxygen. The spectra from the known concentration of oxygen is then compared to the spectra of the cell to determine the oxygen tension present in the cell.

The invention also provides a system for determining oxygen concentrations in biological systems, including (1) physiologically acceptable paramagnetic material in the biological system, and (2) an EPR spectrometer to determine the EPR spectra of the biological system. The paramagnetic material can include India ink, an ingredient of India ink having physiologically acceptable paramagnetic quality, carbon-based material, and carbon black. The biological system can be in vitro and in vivo biological tissue, biological tissue having phagocytic activity, one or more phagocytic cells, living animals and humans. The paramagnetic material is introduced to the biological system via an appropriate manner, including: direct injection into the biological system; direct injection into the blood stream; via lymphatics; and through ingestion.

Preferably, in another aspect, the system includes means for determining the peak-to-peak line width of the EPR spectra. This line width is then compared with the peak-to-peak line width of the EPR spectra of the paramagnetic material in the presence of a known concentration of oxygen. A system according to the invention also preferably includes a magnet, for applying a magnetic field to the biological system, and means for sweeping the magnitude of the magnetic field between approximately 100 and 500 Gauss. The magnitude is typically varied in a period less than sixty seconds.

In another aspect, a system according to the invention includes means, e.g., a magnet or an electromagnet, for applying a first magnetic field to the biological system that has lines of force in substantially one direction. The system further has means, e.g., a magnet or an electromagnet, for generating a second magnetic field with lines of force substantially parallel to the first magnetic field to modify and sweep the magnitude of the first magnetic field between approximately .1 and 500 Gauss. Preferably, the system has means for generating a third magnetic field, with lines of force substantially perpendicular to the first magnetic field, wherein the third magnetic field is modulated between approximately 1 and 500 kHz to improve the signal-to-noise ratio of the measured spectra.

In still another aspect, the system has an oscillating electromagnetic source for applying electromagnetic radiation to the biological system. The electromagnetic radiation, preferably within the range 100 MHz to 5 GHz, such as the L-band microwave frequencies, is directed to the biological system and is substantially perpendicular to the magnetic field.

In still another aspect according to the invention, the EPR spectrometer has a resonator and means for determining the resonator Q. Preferably, the resonator Q is compensated in response to movements of the biological system to maintain the resonant frequency.

In other aspects, the paramagnetic material of the system is substantially uniform, with particle diameters between approximately 0.1 micron and 100 microns. The paramagnetic material can also be one or more relatively large particles with diameters between approximately 100 microns and one centimeter. These relatively large particles function much like a point source for the spectra in the biological system. In one aspect, for example, the paramagnetic material is localized within the biological system, thereby providing a selectable spatial indication of the oxygen tension in the biological system.

In other aspects, the system provides means to determine the EPR spectra directly from the surface of the biological system, e.g., the skin of a human. If the biological system is biological tissue having a circulatory blood flow, the system can include means for changing the blood flow to the tissue and means for determining the change in the EPR spectra, thereby providing a real-time evaluation of the change in oxygen concentration in the tissue. Accordingly, the system can also include means, e.g., a tourniquet, for reducing the blood flow to the tissue to reduce the oxygen concentration at the tissue.

The invention also provides, in another aspect, a spectrometer for the in vivo measurement of oxygen concentration in tissue. The spectrometer includes (1) magnets for selectively applying a magnetic field of selectable strength to the tissue, (2) electromagnetic oscillator for selectively applying electromagnetic radiation having a frequency between approximately 100 MHz and 5 GHz to the tissue, (3) detector for detecting the electron paramagnetic spectra of the tissue, (4) resonator arranged to maintain a substantially constant resonant frequency, (5) console in communication with the detector for displaying the EPR spectra, and (6) computer connected to the console for controlling the spectrometer, and for analyzing the EPR spectra.

Preferably, the resonator includes an automatic frequency control circuit to tune the resonator to the frequency of the oscillator. The detector is preferably arranged with a preamplifier for combined, high-dynamic range detection of EPR spectra.

In other aspects, the spectrometer includes an electromagnetic bridge with automatic frequency control, a fixed frequency oscillator, and a varactor diode tuned resonator. The electromagnetic bridge, especially in the microwave region, is arranged to tune the resonator to the resonant frequency, thereby compensating for movements of the tissue. In another aspect, the resonator has a high Q LC circuit coupled with an external planar loop via a λ/2 symmetrical line. Further, the computer can be arranged for (1) determining the peak-to-peak line width of the EPR spectra, (2) storing calibration EPR spectra of paramagnetic material in the presence of known concentrations of oxygen, and (3) comparing calibration spectra with EPR spectra of the tissue.

In a preferred aspect, the spectrometer system comprises India ink, a constituent of India ink having physiologically acceptable paramagnetic quality, or other physiologically acceptable paramagnetic materials, in the tissue to be measured.

The methods of the invention preferably utilize an EPR spectrometer constructed in accordance with the invention, such that the EPR spectra is determined without significant interference from the configuration or movement of the biological system; and further such that the measurement is compatible with EPR spectra from physiologically acceptable paramagnetic materials, e.g., India ink, in in vivo tissue.

These and other aspects and advantages of the invention are evident in the description which follows and in the accompanying drawings.

DETAILED DESCRIPTION OF THE INVENTION

The invention concerns apparatus, systems, and methods for determining the partial pressure of oxygen, $pO_2$, in biological systems, including in vivo or ex vivo tissue. The invention provides improvements to EPR oximetry by improving the sensitivity, accuracy, and repeatability of EPR techniques. The invention further provides an EPR spectrometer and a paramagnetic material that are physiologically compatible with in vivo measurements. This paramagnetic material is already approved for use with humans; and the material exhibits a measurable correlation between EPR spectra and oxygen tension over a clinically effective pressure, sensitivity, and resolution range. These methods, systems, and apparatus have immediate and important application to clinical and experimental problems which exist today.

The invention utilizes physiologically acceptable paramagnetic materials, and in particular carbon black, especially in the form of India ink, as new paramagnetic probes for EPR oximetry. India ink is an injectable compound that is widely used in clinical settings, with no apparent toxicity. India ink has extensive prior use in humans as the basis for black tattoos, used for medical purposes as well as for personal decoration. It has also been widely used in surgery to trace pathways in tissues. India ink additionally exhibits the desired physical and chemical properties required for effective clinical EPR oximetry, having EPR spectra that is very sensitive to the presence of oxygen. In accordance with the invention, physiologically acceptable paramagnetic materials— such as India ink, constituents of India ink, carbon black, or carbon-based material—are used to directly determine the $pO_2$ in biological systems, such as tissue. Previously, no known paramagnetic material has exhibited the requisite properties to enable direct, in vivo evaluation of humans.

The description below discusses the relevant properties of India ink, and the methodology and apparatus for determining $pO_2$ in vivo via EPR oximetry. Experimental results are given from tests conducted with live animals, and from tests demonstrating that oxygen dependent changes in India ink EPR spectra can be detected in humans. The latter experimental results are based upon the presence of India ink within an ornamental human tattoo, and the response of India ink EPR spectra to differing oxygen concentrations present at the tattoo.

Figure 1A:
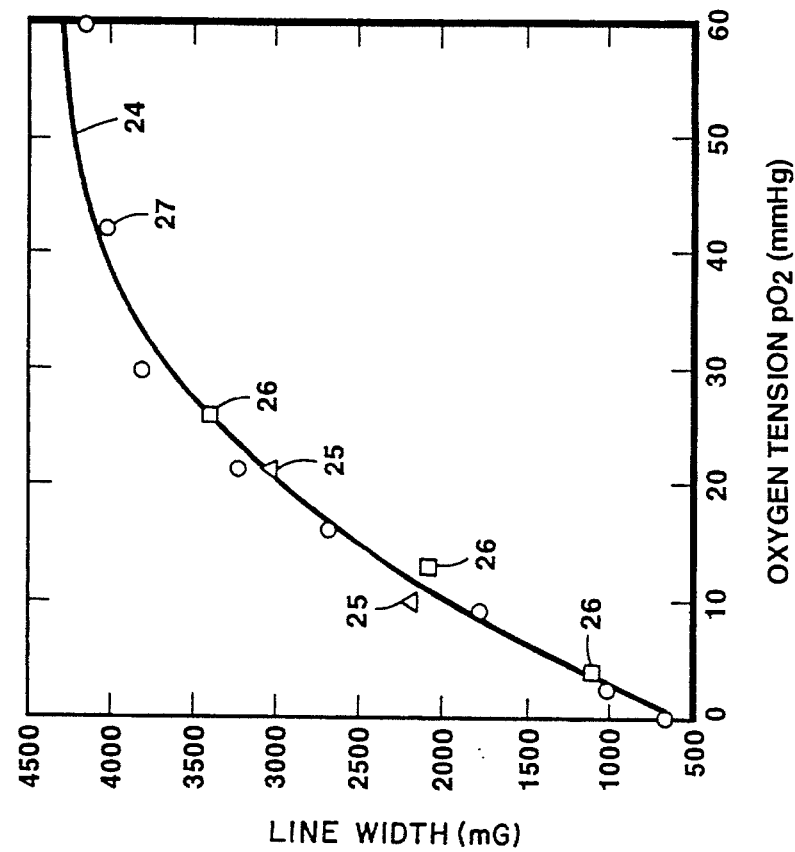
FIG. 1A graphically shows EPR line width spectra from India ink in the presence of other materials, such as water, serum and oleic acid.
Figure 1:
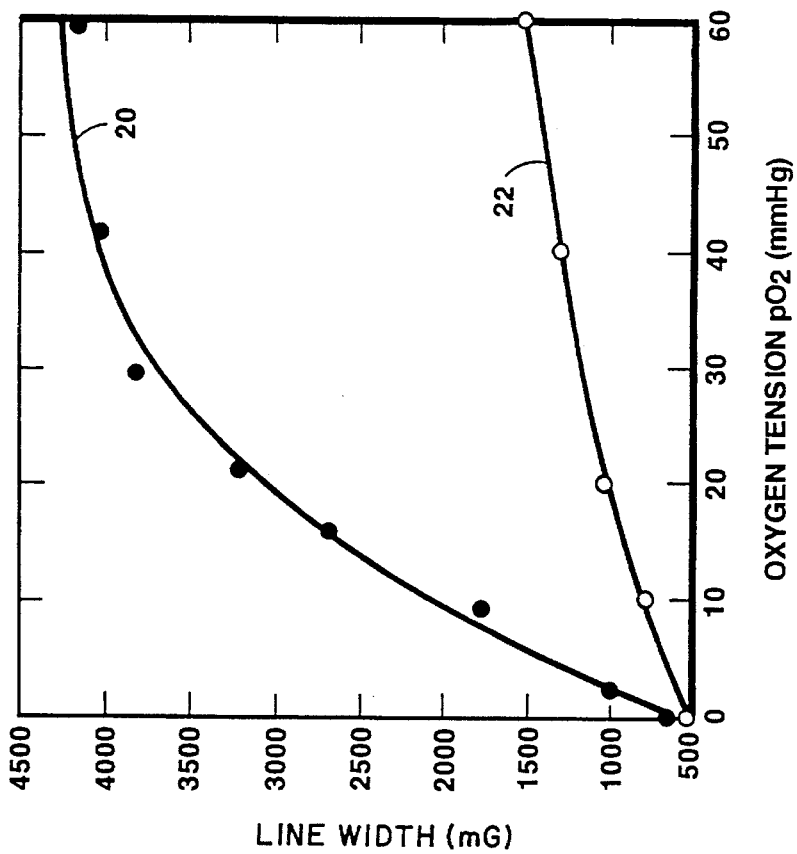
FIG. 1 graphically shows calibration EPR line width spectra of India ink and Fusinite over a wide range of oxygen tensions.

India ink is a stable paramagnetic material. It has a single EPR signal spectra with a peak-to-peak line width that is calibrated to directly determine oxygen tension $pO_2$ in vivo. FIG. 1 illustrates one set of calibration data in a graph of the EPR spectra line width of India ink 20 and Fusinite 22 against $pO_2$. With reference to FIG. 1, the India ink line width 20 is approximately 600 mGauss in the absence of oxygen and approximately 4500 mGauss in the presence of air. When India ink is within biological tissues, the shape of the EPR spectra is between these values, which is correlated to determine the in vivo oxygen tension. On the other hand, over the same partial pressures, the Fusinite line width only changed from 500 mGauss at 0 mm Hg to 1200 mGauss at 35 mm Hg.

At least two other noteworthy characteristics are apparent with reference to FIG. 1: first, the India Ink line width spectra is sensitive to oxygen tension levels below 1 mm Hg; and secondly, the slope of the India Ink calibration data 20 shows that the EPR spectra line width is particularly sensitive to changes in oxygen tensions of less than 30 mm Hg, which is a critical realm for effective oxiometric measurements. As compared to fusinite 22, for example, the line-broadening effects of the India ink EPR spectra per unit $pO_2$ are greater, improving sensitivity.

India ink is additionally less sensitive to the external conditions, and to the compounds present in the biological system under investigation, which might otherwise affect or reduce measurement accuracy. Over the broad range of conditions that can occur in vivo, for example, the response of India Ink EPR spectra to $pO_2$ is essentially independent of pH, oxidants, reductants, and the nature or lipophilicity of the biological medium. FIG. 1A graphically shows the line width of India ink EPR spectra 24 in the presence of various media, including oleic acid 25, serum 26, and water 27. The data 24 is the same as the calibration data 20 of FIG. 1, to within the accuracy of the measurement.

Figure 1B:
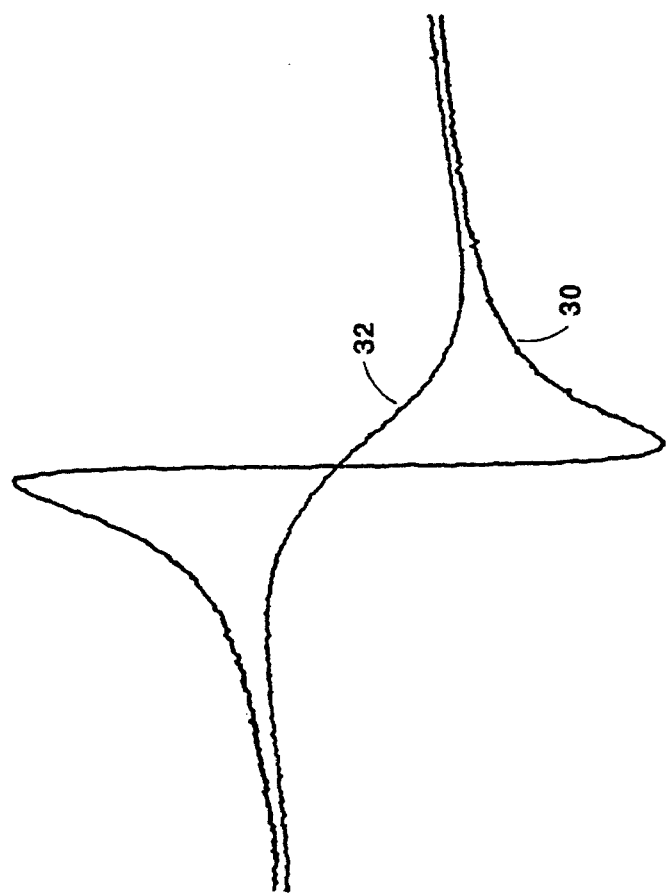
FIG. 1B graphically shows the EPR spectra of India ink in nitrogen and air using a X-band EPR spectrometer.

The experimental India ink data illustrated in FIGS. 1, 1A and 1B, and in the principal experimental data presented in FIGS. 5–8, derive from India ink purchased at SHIKAYA, JAPAN, having a concentration of 80 mg/ml. The India ink particles were homogenous in size, and were approximately 1 µm in diameter. Other chemicals for the principal experiments discussed herein were purchased from Sigma, in St. Louis, Mo.

The calibration of India ink and other in vitro experimental studies of India ink were performed on a Varian E-109 EPR spectrometer, which has an X-band, 9.6 GHz microwave oscillator. Typical control settings for the Varian spectrometer were: (1) 3210 Gauss of magnetic field strength; (2) 10 mW of microwave power; and (3) a modulation amplitude less than one third of the line width. Experimental temperatures were controlled with a Varian gas flow variable temperature control unit. And EPR spectra were collected using EW software, from Scientific Software Inc., in Normal, Ill., which was installed on an IBM-compatible personal computer. DPPH was used as a secondary standard for spin density measurements.

More particularly, the calibration of India ink was as follows. Ten micro-liters of India ink in PBS was drawn into a gas permeable teflon tube from Zeus Industrial Products, Inc., in Raritan, N.J. This teflon tube had a 0.623 mm inner diameter and a 0.138 wall thickness, and was folded twice and inserted into a quartz EPR tube open at both ends. The sample was then equilibrated with different $O_2$: $N_2$ gas mixtures. $pO_2$ in the perfusing gas was monitored and measured by a modified Clark electrode oxygen analyzer from Sensor Medics Co., Model OM-11, in Anaheim, Calif., which was calibrated with pure air and nitrogen. FIG. 1B shows that the response of the India ink EPR line width spectra 30 in air, as compared to the spectra 32 in nitrogen, is severe, indicating the ink's usefulness for oximetry.

The quantitative dependence of the EPR spectra on $pO_2$ was obtained by measuring the line width as a function of $pO_2$ in the perfusing gas. EPR line widths are usually reported as the difference in magnetic field between the maximum and minimum of the first derivative recording of the signal. In other words, the EPR line width is the peak-to-peak separation of the first derivative, with respect to frequency, of the Lorentzian-shaped absorption spectra.

Figure 2:
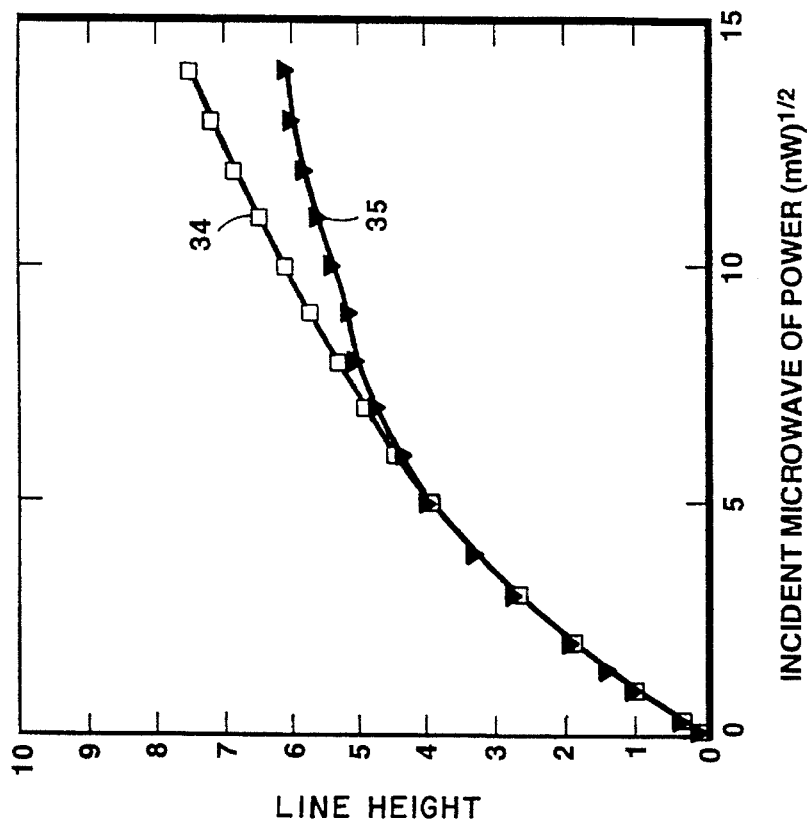
FIG. 2 graphically shows microwave power and saturation data on line height in nitrogen and in air.

The experiments presented herein also considered the microwave saturation effects of the environment. FIG. 2 summarizes microwave power data on the line height within nitrogen 34 and air 35. Because power saturation occurred only at high microwave powers, the in vitro experimental testing utilized 10 mW of unsaturated X-band microwave radiation.

With further reference to FIGS. 1 and 1A, the g-value, spin density, and line width of the EPR India ink spectra were measured at room temperature. The g-value ($2.0027 \pm 0.0008$) and spin density ($2.5 \times 10^{19}$ spin/g) of India ink were not affected by oxygen. While the g-value of India ink was approximately equal to Fusinite, the number of spins for India ink spectra was more than twice the number of spins for Fusinite ($1.0 \times 10^{19}$ spin/g). As illustrated in FIG. 1, the India ink EPR probe is very sensitive, as compared to Fusinite, at low $pO_2$, especially less than 30 mm Hg of oxygen tension. Conveniently, the principal $pO_2$ dependencies for clinical and biomedical applications occur in the range of 0–30 mm Hg $pO_2$, making India ink EPR oximetry a valuable measurement tool.

India ink EPR spectra exhibited no self-broadening due to changes in the concentration of India ink particles. No effect, for example, was observed in the EPR spectra of India ink in the presence of a paramagnetic agent, $K_3Fe(CN)_6$, an oxidant, $H_2O_2$, or a reductant, ascorbic acid. The line width of India ink was also not affected by variation in temperatures between 25° C. and 50° C., nor by variations in the pH between 4 to 14. FIG. 1A illustrates that the response of EPR India ink spectra in the presence of oxygen is essentially independent of the media, including oleic acid 25, serum 26, and water 27.

For in vivo EPR measurements, discussed below, an EPR spectrometer constructed in accordance with the further features of the invention was utilized, having a L-band, low-frequency microwave oscillator (approximately 1.2 GHz) with an extended planar loop antennae connected to a resonator.

Figure 3:
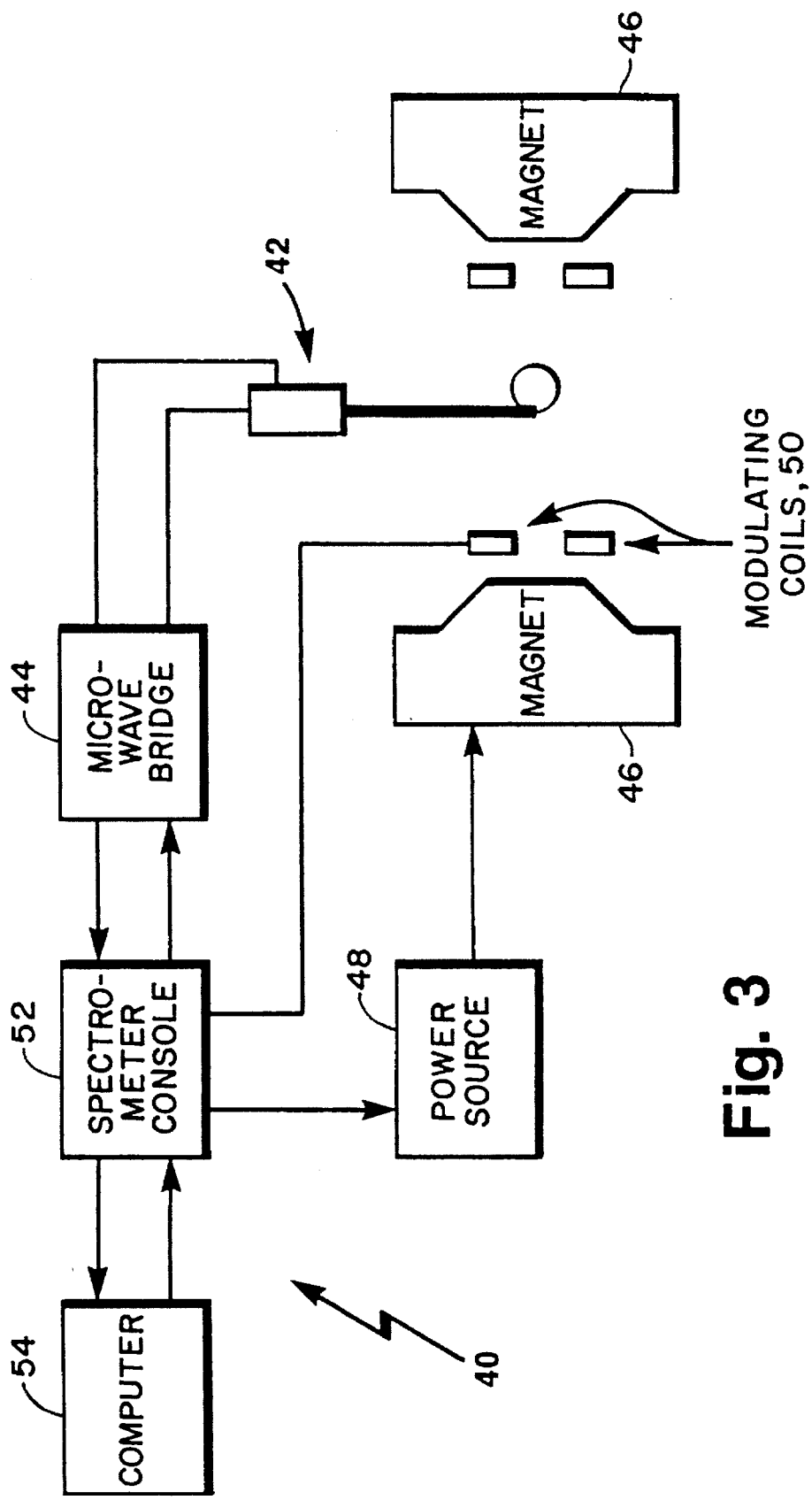
FIG. 3 is an EPR spectrometer constructed in accordance with the invention.
Figure 4:
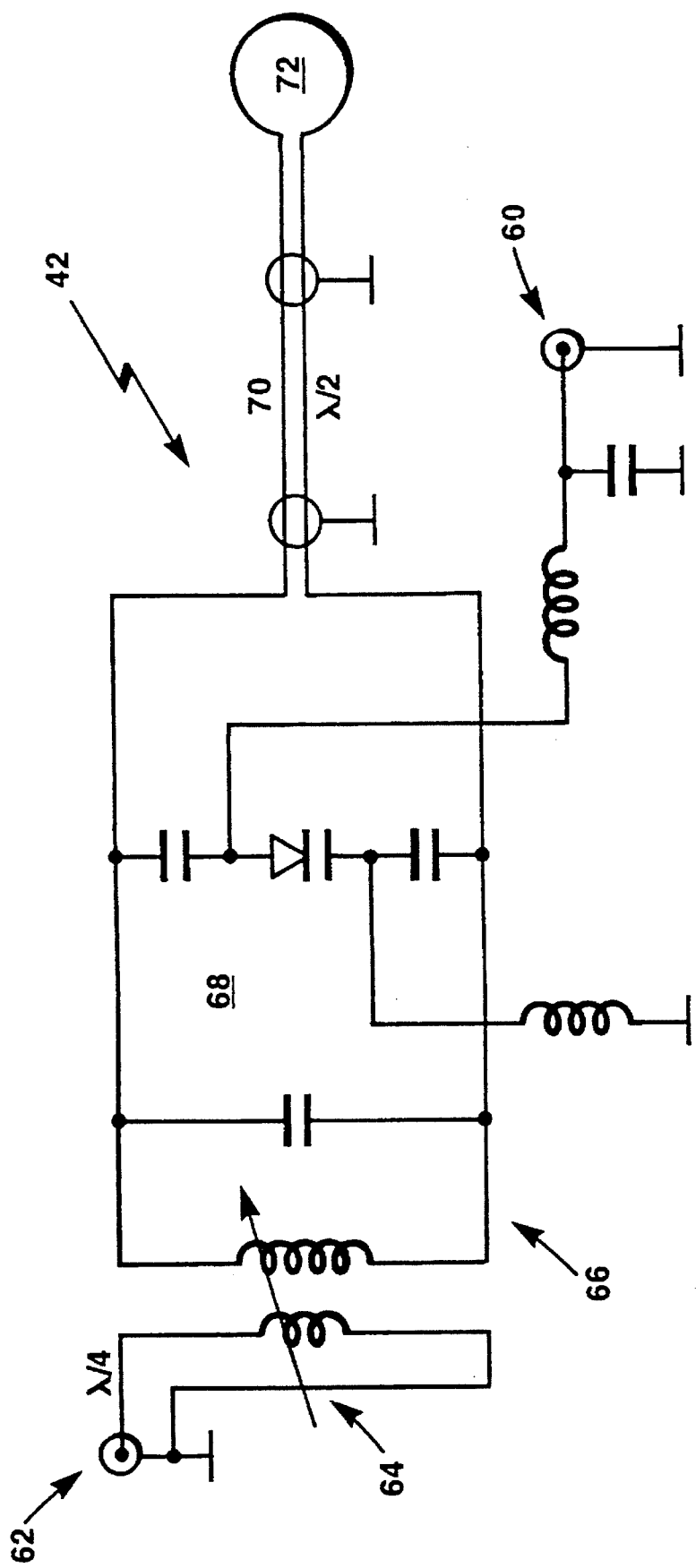
FIG. 4 is a microwave resonator for use in the EPR spectrometer of FIG. 3.

FIGS. 3 and 4 illustrate an EPR spectrometer apparatus 40 constructed in accordance with the invention, and which has significant structural differences as compared to conventional EPR spectrometers. Most significantly, the spectrometer 40 permits the accurate measurement of EPR spectra from in vivo biological systems, such as live animals, by retuning its resonator 42 to maintain resonant frequency during movements of the animal.

A spectrometer 40 constructed according to the invention solves certain technology problems which make existing EPR spectrometers incompatible with oxiometric measurements using physiologically acceptable paramagnetic materials. Existing EPR spectrometers are especially incompatible with in vivo measurements of live beings using paramagnetic probes either implanted in tissue or administered through another route, such as orally, intravenously, or by injection.

The spectrometer system 40 is a low frequency EPR spectrometer that measures the EPR spectra of India ink or other physiologically acceptable materials in animals, including humans, and other biological systems. The spectrometer 40 has a resonator 42 and an associated microwave bridge 44. The spectrometer 40 further has a magnet 46, powered by a power supply 48, and modulation coils 50. The power supply 48, the coils 50, and the microwave bridge 44 connect to a standard spectrometer console 52. A computer 54 connects to the console to control elements in the spectrometer 40.

In a conventional microwave bridge for an EPR spectrometer, an Automatic Frequency Control (AFC) circuit locks the microwave oscillator to the resonant frequency of the resonator. This is problematic for the purpose of measuring animals, or a patient, with EPR oximetry. Movements in the subject being studied cause a retuning of the oscillating bridge frequency by $\pm 5$ MHz, which is equivalent to a shift in the position of the EPR line width by 2000 mGauss. In the spectrometer 40 of FIGS. 3 and 4, the AFC circuit has been constructed so that the resonator is tuned to the microwave source, using a varactor diode with a range of approximately $\pm 8$ MHz. Consequently, the microwave frequency is stable and independent of movement of the experimental subject, tissue, or being under investigation.

In operation, and with reference to FIG. 3, the magnet 46 applies a magnetic field to the subject under investigation, which is adjacent to the resonator 42. This magnetic field aligns and separates spins of unpaired electrons of the subject within the field so that microwave energy is absorbed by the subject's molecules. The microwave bridge oscillator 44 and resonator 42 jointly apply a microwave electromagnetic field to the subject while maintaining a single resonant microwave frequency in the high Q resonator circuitry, illustrated in FIG. 4. The microwave energy is absorbed by the molecules according to a functional dependence with the magnetic field strength. At one magnetic field strength, the photon energy of the microwave field is matched to the excited molecular state of the electron spins, and peak absorption is attained. Other frequencies of the EPR resonance are attained by gradually changing, or "sweeping", the strength of the magnetic field generated by the magnet 46. At the other frequencies, the microwave absorption is less. A full sweep by the magnet 46 generates an absorption spectra having a Lorentzian line-shape, or, more typically, spectra presented as the first derivative of that line shape.

The presence of oxygen in a subject or tissue having a physiologically acceptable paramagnetic material, e.g., India ink, affects the relaxation rate of the excited paramagnetic molecule, thus causing an increased time-integrated intensity, or line-broadening effect within the spectra, as discussed above.

FIG. 4 illustrates the external loop resonator 42 constructed in accordance with the invention and which improves oscillator stability and sensitivity for possible resonant mismatching caused by movements of the biological tissue. The resonator 42 includes an input 60 for Automatic Frequency Control (AFC) circuitry, a high frequency input 62 for a 50 Ω coaxial line, and a variable inductive coupling 64. The resonator 42 further has a high Q LC resonant circuit 66, a varactor diode 68, a two-wire λ/2 symmetrical line 70, and a planar loop 72.

The resonator 42 avoids the physical access problems faced by conventional EPR spectrometers in co-locating the resonator and subject within a common magnetic field. The resonator 42 matches and maintains the resonant frequency of the resonator cavity by use of a high Q LC circuit 66 coupled with an external planar loop 72 via a λ/2 symmetrical antenna-like line. The LC circuit 66 is matched to a 50 Ω coaxial line at the input 62 via a variable inductive coupling 64. The coupling 64 consists of a coupling loop, a λ/4 flexible impedance transformer, and a mechanism that changes the position of the loop relative to the LC circuit 66. The application of the impedance transformer makes it possible to effectively match the resonator to the 50 Ω line. The loop portion 72 is the antennae-like element which is placed in proximity to the region to be studied. The loop 72 can be configured to optimally fit the subject, e.g., by going around a protruding tumor, because the resonator need not be in the magnetic field. This is not, however, how a conventional resonator operates, where the subject and the resonator are within a common magnetic field, thereby constraining measurement flexibility.

Movement of the subject also influences the resonator's match to the 50 Ω coaxial line, which increases the high frequency voltage level at the output. This could potentially produce an overload of the preamplifier and detector, and, therefore, the spectrometer 40 of FIG. 3 preferably utilizes a wide-dynamic preamplifier and detector to measure the EPR absorption spectra.

The spectrometer 40 described in FIGS. 3 and 4 also operates at a lower frequency than conventional EPR spectrometers. Typically, conventional systems have oscillating frequencies of approximately 9 GHz, which are strongly absorbed by high dielectric materials such as water or tissue. Microwave absorption at 9 GHz operates much like a microwave oven, creating unwanted heating in clinical applications. Thus, the spectrometer 40 of FIG. 3 operates with a lower frequency microwave oscillator. One acceptable frequency range used is within L-band frequencies, i.e., 1100–1200 MHz, which provide an acceptable compromise between depth penetration and sensitivity. L-band microwave frequencies are suitable for paramagnetic probes, such as India ink, located at depths of up to ten millimeters.

However, as those skilled in the art can appreciate, the spectrometer 40 is easily constructed according to the invention at lower frequencies, such as within the radiofrequency range of 100 to 1000 MHz, to increase penetration depth while decreasing sensitivity, which may be desirable in some applications.

Those skilled in the art also understand the principal operation of the other components of the spectrometer 40, FIG. 3, and of other essential components not illustrated, as they are functionally similar to comparable, conventional EPR spectrometer components.

The advantages provided by the spectrometer 40 in the context of EPR oximetry using paramagnetic probes are several. First, the spectrometer 40 attains maximum possible depth within the target tissue while retaining sufficient sensitivity for accurate and rapid clinical and biological applications. The spectrometer 40 further is unaffected by the particular dimensions of the target tissue, or body, to be studied because the resonator 42 is not limited by the configuration of the resonant structure employed as the detector. Finally, the inevitable motions of living animals, e.g., heart beats, respiration, and small physical movements, are compensated by adjustments to the resonator frequency to maintain a balanced bridge.

Thus, the spectrometer 40 of FIG. 3 is especially well-suited for EPR measurements of animals or patients when combined with the properties of physiologically acceptable paramagnetic materials, such as India ink. This combination in accordance with the invention is suitable for many clinical and experimental uses for the direct measure of $pO_2$ in in vivo tissues.

In vivo measurements were first conducted in the gastrocnemius muscles of adult mice. A 10 μl slurry of India ink was injected into these muscles, whereafter the animals were measured for EPR spectra by an EPR spectrometer, such as the spectrometer 40 of FIG. 3. The coupled planar loop antennae 72, FIG. 4, was positioned over the area of the leg containing the India ink. When required, blood flow was restricted by a ligature around the upper leg. The animals were conscious throughout the experiment.

Figure 5:
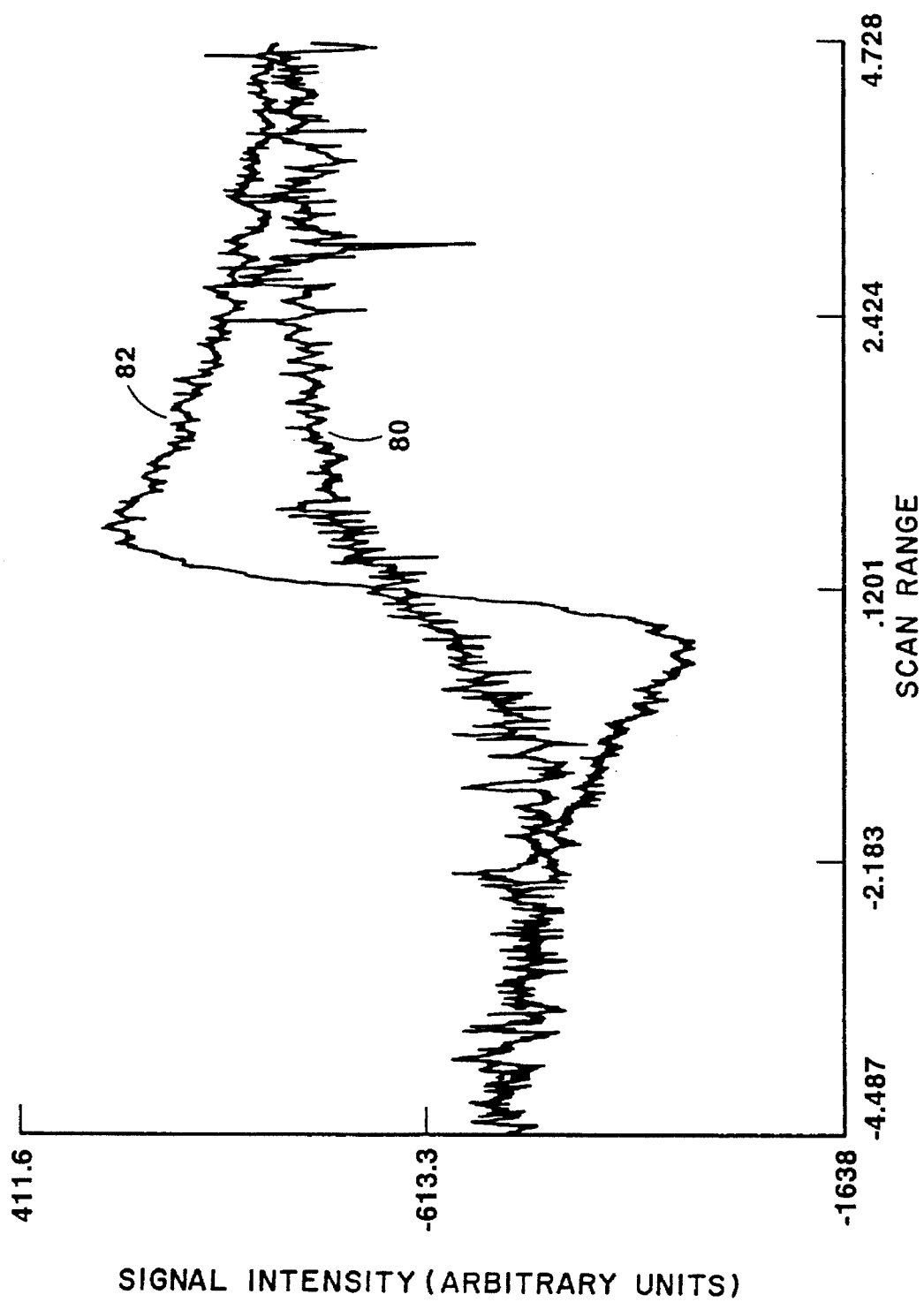
FIG. 5 shows the signal response of EPR India ink spectra before and after restricting the blood flow to the gastrocnemius muscles of an adult mouse injected with India ink.

The stability of the response of India ink EPR spectra to oxygen concentration in the mice was studied by measuring the EPR spectra before and after restricting the blood flow. FIG. 5 shows the EPR signal spectra 80 of India ink-injected gastrocnemius muscle of the mouse with unrestricted blood flow one day after implantation. When blood flow to the leg was restricted by a ligation around the upper leg, the EPR spectra response to a reduction of $pO_2$ is indicated by the narrowing line width and increased line height, as shown by the signal spectra 82. The corresponding $pO_2$ before and after the constriction of the blood flow were 11.4 mm Hg and 0.7 mm Hg, respectively.

Figure 7:
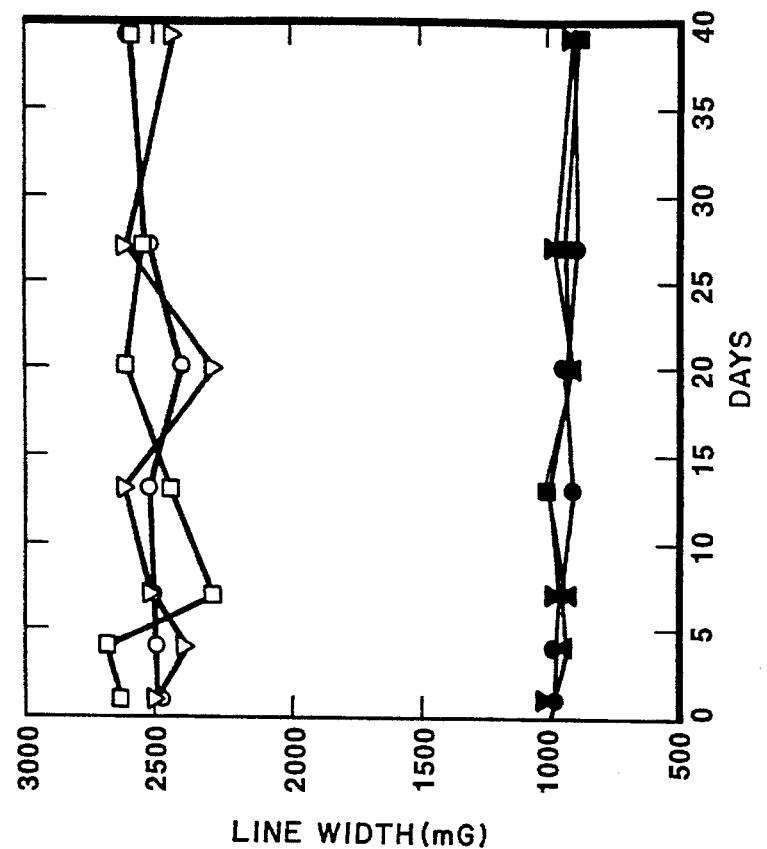
FIG. 7 graphically shows the de-oxygenation characteristics of mouse muscle injected with India ink over a period of thirty-nine days.
Figure 6:
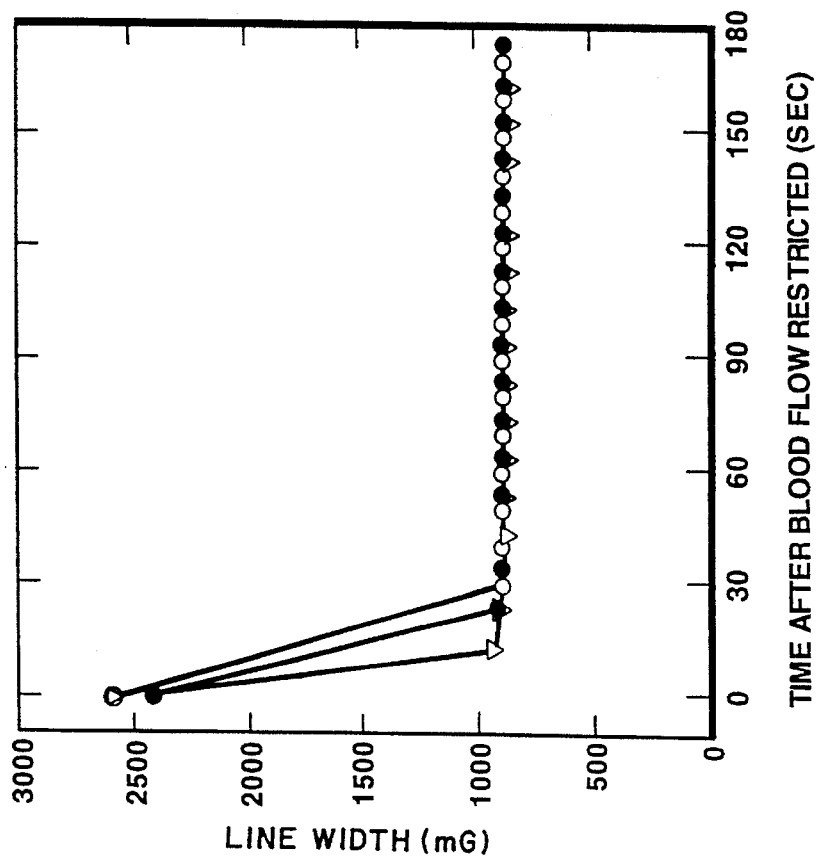
FIG. 6 graphically shows the de-oxygenation in in vivo mouse muscle injected with India ink, subsequent to the tightening of a tourniquet.
Figure 8:
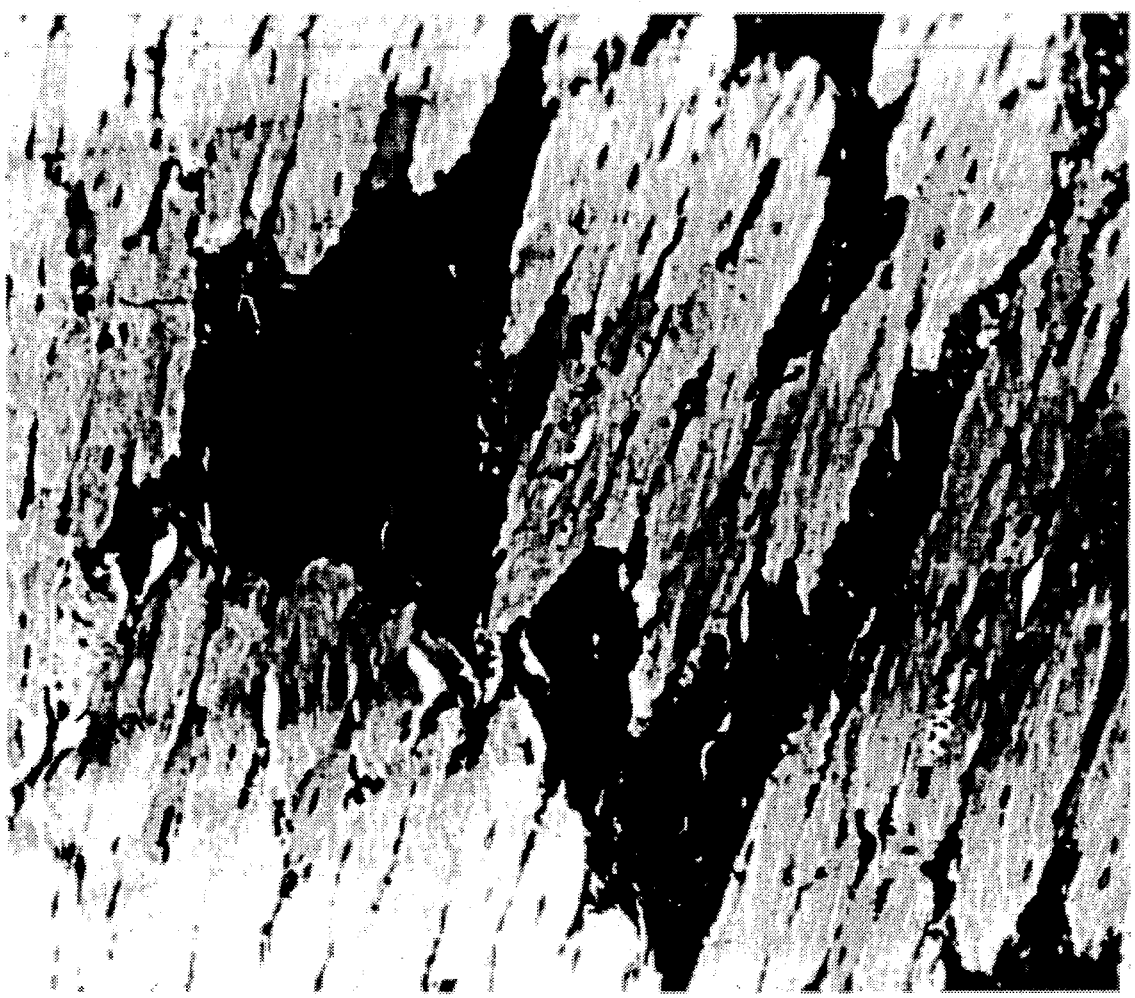
FIG. 8 shows a histological slide of mouse leg muscle forty days after implantation by India ink.

The kinetics of de-oxygenation in in vivo mouse muscle, subsequent to the tightening of the tourniquet, was also monitored. FIG. 6 graphically shows that the response of India ink is sufficiently rapid to follow the de-oxygenation, typically within 20 seconds. This response lasted for at least thirty-nine days, as shown by the periodic experimental data of FIG. 7, with little resultant toxicity, as shown in FIG. 8. The upper data points of FIGS. 6 and 7 represent unrestricted oxygen flow to the muscle; while the lower data points represent restricted oxygen flow. The multiple, co-located data points represent the several mice tested.

FIGS. 6–8 illustrate the very favorable biological properties of India ink, including stability, FIG. 7, low toxicity, FIG. 8, and the rapid response of the spectra to changes in $pO_2$, FIG. 6. Once India ink is injected into the tissue of interest, $pO_2$ is measured conveniently, rapidly, and repetitively in a non-invasive manner, i.e., through EPR oximetry. The enormous sensitivity of carbon-based materials, such as India ink, to oxygen, combined with its inert physical and chemical properties, make carbon-based physiological paramagnetic materials ideal probes for oxygen measurements in tissues, including that of animals and humans. The paramagnetic material preferably has a substantially uniform particle size having diameters ranging between about 0.1 μm and about 100 μm. The material also preferably includes one relatively large particle having a diameter ranging between about 100 μm and about 1.0 cm.

India ink, being clinically approved material, can immediately be used within humans to measure oxygen concentrations in clinical settings. The EPR spectrometer constructed according to the invention, e.g., the spectrometer 40 of FIG. 3, with the external loop resonator and microwave bridge, provides clinically effective EPR spectra measurement capability from paramagnetic materials in living experimental animals and human subjects. The whole process of measurement in accordance with the invention takes less than 30 seconds.

The invention offers the additional advantage of providing spatially resolved information of $pO_2$ directly, because the measured EPR spectra is detected at the specific point where the India ink is inserted. This technology is expandable, in accordance with the invention, for the simultaneous measurement of $pO_2$ at two or more test sites. A single particle of India ink can also be inserted at a selectable spatial location within the biological system or tissue to provide a selectable and spatial test probe within the system. The particle is selected according to the test biological system and can be cellular in size, e.g., 0.1 μm, or relatively large in size, e.g., one centimeter. By inserting such a particle to the system, the EPR spectra is measured from a selectable and localized region in the biological system, such as within a cell or within the liver.

Figure 9:
FIG. 9 illustrates the tattoo of a human volunteer.
Figure 10:
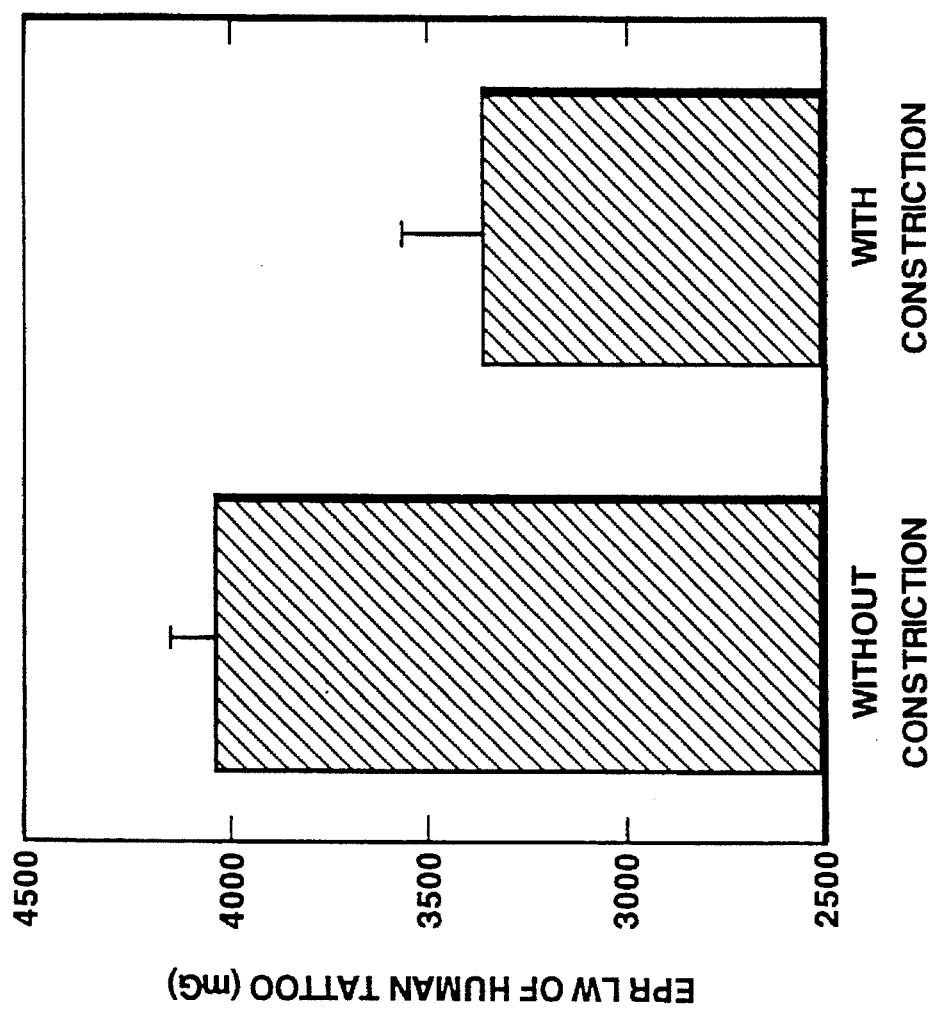
FIG. 10 graphically shows EPR spectra from a human tattoo based on India ink with and without blood flow restriction.

EPR oximetry in vivo measurements of a human subject injected with physiologically acceptable paramagnetic materials were performed through use of an extensive tattoo, illustrated in FIG. 9, comprising India ink. The human subject was a volunteer who had the tattoo on his forearm. Accordingly, the EPR spectra of the tattoo indicated the oxygenation of the skin. Similar to the experiments conducted on the mice, EPR spectra measurements were made of the tattooed skin before and after constricting the blood flow to the forearm. FIG. 10 graphically shows the India ink EPR spectra line width variation due to the constriction of the blood flow, providing a direct measurement of $pO_2$.

The particular details of the measurements in FIG. 10 are as follows. The forearm with the tattoo was placed between the poles of a magnet of an L-band microwave spectrometer constructed in accordance with the invention, such as described in FIG. 3. A prominently black area of the tattoo was positioned on the detector and spectra were obtained before and during constriction of the blood flow by means of a rubber tourniquet around the arm and above the tattoo. When the blood flow was restricted, the EPR spectra line width narrowed while its line height increased. The line width changed from 4050 mGauss, unrestricted, to 3400 mGauss, restricted.

Methods and apparatus for determining oxygen concentration in tissue having one or more of the foregoing features according to the invention have several advantages. These include the ability to directly determine oxygen concentration in in vivo tissues in order to assess their state and response to therapy. This capability is especially desirable for planning, and for evaluating tumor therapy and vascular insufficiency. Furthermore, the sensitive, accurate, and repeated measurements of $pO_2$ in tissues provided for by the invention has clinical significance, especially for the optimization and utilization of cancer therapy, and for the diagnosis and treatment of vascular disease. A number of other potential clinical applications, including the evaluation of other diseases which concern oxygen pressure within tissues can also benefit from the invention by providing clinically useful information. The modern hospital may eventually utilize the teachings of the invention in an integral clinical role, especially in the oncology and cardiovascular sections of the hospital.

The invention further provides for a wide range of experimental studies that may be undertaken in small and large animals. These studies include the clinical areas described above, and may further include a wide range of studies in basic biology and physiology, because of the importance of oxygen concentrations in most physiological and pathophysiological processes. The results presented herein, particularly from the EPR studies of India ink in mice and humans, additionally indicate that methods and apparatus in accordance with the invention achieve good signal-to-noise ratios and repeatable in vivo EPR measurements, often without anesthesia. The availability and safety of the paramagnetic India ink material provide for the immediate and in vivo usage of these methods in animals and humans.

India ink has been extensively used in patients as a marker for surgical procedures and radiation therapy, in addition to its extensive non-medical use for decoration. In general surgery, India ink has been used to mark surgical resection margins. For example tattooing with India ink has been described as a precise and practical method for identifying a biopsy site when there is significant delay between biopsy and definitive surgery. E. Epstein, J. Dermatol, *Surg. Oncol.* 15, 272 (1989). India ink has also been used to indicate the location of lymph nodes and lymphatic channels. For example, Maruyama et al., *Nippon Geka Gakkai Zasshi* 901, 318 (1989), injected India ink in the perigastric lymph nodes of 3,785 patients who had stomach cancer at the operation in order to find metastatic lymph nodes and reported that this technique made it easier to find lymph nodes, thereby improving prognoses. In radiation therapy, India ink is routinely used to mark fields for irradiation. For example, S. J. Walker, *Radiography Today* 54, 617 (1988), made a survey of methods for marking fields in twelve radiotherapy centers in Britain, and reported that tattooing with India ink was a standard procedure in most departments. There was no suggestion of any serious problems in tattooing. In the endoscopic field, India ink is used as a long-term colonic mucosal marker. Fennerty et al., *The American Journal of Gastroenterology* 87, 79 (1992), implanted India ink tattoos to colorectal polygas of patients who were followed for at least six months, and reported no side effects or complications.

The basis for the apparent lack of toxicity of India Ink is fairly straight-forward. India ink consists of a suspending vehicle, an emulsifier, and the "active ingredient", which is carbon black. From analyses of its physical properties, and from experience in animals and patients, the carbon black appears to be both non-reactive and non-allergenic. The particles of India ink are also very small, homogenous, and independent from each other. When the ink is injected intravenously, the particles are trapped by the reticuloendothelial system, i.e., the liver and spleen, and not in the capillaries of the lung. In vitro experiments have shown that India ink is easily taken into cells via phagocytosis, without showing any toxicity, as measured by the colony-forming ability and exclusion of trypan blue. Therefore, in accordance with the invention, India ink is also useful for the selective measurement of intracellular $pO_2$.

The invention thus attains the objects set forth above, among those apparent from preceding description. Since certain changes may be made in the above apparatus and methods without departing from the scope of the invention, it is intended that all matter contained in the above description or shown in the accompanying drawing be interpreted as illustrative and not in a limiting sense.

It is also to be understood that the following claims are to cover all generic and specific features of the invention described herein, and all statements of the scope of the invention which, as a matter of language, might be said to fall there between.

Having described the invention, what is claimed and desired to be secured by Letters Patent is:

1. Apparatus for measuring oxygen tension in a biological system having a paramagnetic located therein, comprising (a) magnetic means for selectively applying a magnetic field of selectable strength to the biological system, (b) electromagnetic means for selectively applying electromagnetic radiation having a selected substantially constant frequency to the paramagnetic material in the biological system, (c) detection means for detecting the electron paramagnetic spectra of the biological system, said spectra having a selected peak-to-peak line width that is indicative of said oxygen tension in the biological system, (d) resonator means coupled to the electromagnetic means, said resonator means including means for tuning said resonator means to the constant frequency of said electromagnetic means to maintain a substantially constant resonant frequency in response to movements in the biological system, (e) console means in communication with said detection means for displaying said spectra, and (f) computer means connected to said console means for controlling said apparatus, and for analyzing said spectra to determine said oxygen tension.

2. Apparatus according to claim 1 wherein said detection means includes preamplifier means and a detector for combined, high-dynamic range detection of said electron paramagnetic spectra.

3. Apparatus according to claim 1 wherein said tuning means comprises an automatic frequency control means with a fixed frequency oscillator and a varactor diode tuned resonator.

4. Apparatus according to claim 1 wherein said resonator means comprises a high Q LC circuit coupled with an external planar loop via a $\lambda/2$ symmetrical line.

5. A system for determining oxygen tension within a biological system, comprising means for introducing india ink into the biological system, magnetic means for applying a first magnetic field to the biological system, radiation means for applying electromagnetic radiation having a frequency between about 100 MHz and about 5 GHz to the biological system to excite the india ink to a higher energy state, said excited india ink then relaxing at a rate dependent upon the presence of oxygen in the biological system, and means for determining the electron paramagnetic resonance spectra of the biological system, said spectra being indicative of the oxygen tension within the biological system.

6. The system of claim 5 further comprising means for sweeping the magnitude of said first magnetic field between about 100 Gauss and about 500 Gauss.

7. The system of claim 6 wherein said means for sweeping includes second magnetic means for applying a second magnetic field generally parallel to the first magnetic field to the biological system, and adjusting means for adjusting the intensity of the second magnetic field to vary the magnitude of the first magnetic field.

8. The system of claim 6 wherein said means for sweeping comprises a magnet or an electromagnet.

9. The system of claim 5 further comprising modulation means for generating a third magnetic field generally orthogonal to said first magnetic field, and means for modulating said third magnetic field between about 1 KHz and about 500 KHz.

10. The system of claim 5 wherein said means for determining comprises a resonator having an operating resonant frequency.

11. The system of claim 10 wherein said radiation means applies radiation having a substantially constant frequency, said system further comprising resonant frequency control means for adjusting said resonant frequency of said resonator in response to movements of the biological system to match said constant frequency of said radiation means.

12. The system of claim 5 further including a resonator operable at a selected resonant frequency.

13. The system of claim 12 wherein said radiation means applies radiation having a substantially constant frequency, said system further including tuning means for tuning said resonant frequency of said resonator to said constant frequency of said radiation means to maintain a substantially constant resonant frequency.

14. The system of claim 13 wherein said tuning means includes an automatic frequency control circuit.

15. The system of claim 12 wherein said resonator includes an LC resonant circuit, and an external planar antenna loop in communication with said resonant circuit.

16. The system of claim 15 wherein said resonator further includes a variable inductive coupling and a varactor diode in electrical communication with said resonant circuit.

17. A system for determining oxygen tension within a biological system, comprising means for introducing an electron paramagnetic material into the biological system, magnetic means for applying a magnetic field to the biological system, radiation means for applying electromagnetic radiation having a selected substantially constant frequency to the biological system to excite the paramagnetic material, resonator means operable at a selected resonant frequency, tuning means for tuning said resonant frequency of said resonator to match said constant frequency radiation means to maintain a constant resonant frequency in response to movements in the biological system, and means for determining the electron paramagnetic resonance spectra of the biological system, said spectra being indicative of the oxygen tension within the biological system.

18. The system of claim 17 wherein said electron paramagnetic material comprises carbon black.

* * * * *